United States Patent
Kato

(10) Patent No.: US 9,675,545 B2
(45) Date of Patent: *Jun. 13, 2017

(54) ACICULAR BODY

(71) Applicant: TOPPAN PRINTING CO., LTD., Taito-ku (JP)

(72) Inventor: Hiroyuki Kato, Taito-ku (JP)

(73) Assignee: TOPPAN PRINTING CO., LTD., Taito-ku (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/959,228

(22) Filed: Dec. 4, 2015

(65) Prior Publication Data

US 2016/0081919 A1    Mar. 24, 2016

Related U.S. Application Data

(63) Continuation of application No. PCT/JP2014/064836, filed on Jun. 4, 2014.

(30) Foreign Application Priority Data

Jun. 6, 2013    (JP) ................................. 2013-119915

(51) Int. Cl.

| | | |
|---|---|---|
| A61K 9/00 | (2006.01) | |
| A61K 38/00 | (2006.01) | |
| A61Q 19/00 | (2006.01) | |
| A61K 47/36 | (2006.01) | |
| A61K 8/73 | (2006.01) | |
| A61K 47/48 | (2006.01) | |
| A61K 8/02 | (2006.01) | |
| A61M 37/00 | (2006.01) | |

(52) U.S. Cl.
CPC .......... *A61K 9/0021* (2013.01); *A61K 8/0204* (2013.01); *A61K 8/0216* (2013.01); *A61K 8/736* (2013.01); *A61K 38/00* (2013.01); *A61K 47/36* (2013.01); *A61K 47/4823* (2013.01); *A61Q 19/00* (2013.01); *A61K 2800/91* (2013.01); *A61M 2037/0046* (2013.01); *A61M 2037/0053* (2013.01)

(58) Field of Classification Search
CPC ........... A61M 2037/0046; A61K 47/36; A61K 38/00; A61K 8/736; A61Q 19/00
See application file for complete search history.

(56) References Cited

U.S. PATENT DOCUMENTS

| | | | |
|---|---|---|---|
| 5,463,022 A | 10/1995 | Inoue et al. | |
| 7,789,733 B2 | 9/2010 | Sugimura et al. | |
| 8,292,696 B2 | 10/2012 | Sugimura et al. | |
| 8,377,364 B2 | 2/2013 | Shiomitsu et al. | |
| 8,876,575 B2 | 11/2014 | Sugimura et al. | |
| 9,238,384 B2 | 1/2016 | Shiomitsu et al. | |
| 2008/0200883 A1 | 8/2008 | Tomono | |
| 2008/0208134 A1 | 8/2008 | Tomono | |
| 2008/0262444 A1 | 10/2008 | Takada | |
| 2008/0311223 A1 | 12/2008 | Allen et al. | |
| 2009/0131887 A1 | 5/2009 | Shiomitsu et al. | |
| 2009/0143749 A1 | 6/2009 | Sugimura et al. | |
| 2009/0292254 A1 | 11/2009 | Tomono | |
| 2009/0292255 A1 | 11/2009 | Tomono | |
| 2010/0185162 A1 | 7/2010 | Shiomitsu et al. | |
| 2010/0198169 A1 | 8/2010 | Sugimura et al. | |
| 2010/0203163 A1 | 8/2010 | Allen | |
| 2010/0286079 A1* | 11/2010 | Badwan ............... | A61K 9/0019 514/42 |
| 2010/0316715 A1 | 12/2010 | Andersson | |
| 2012/0016309 A1 | 1/2012 | Binks et al. | |
| 2013/0030374 A1 | 1/2013 | Sugimura et al. | |
| 2013/0140267 A1 | 6/2013 | Shiomitsu et al. | |

FOREIGN PATENT DOCUMENTS

| | | |
|---|---|---|
| EP | 2 062 611 A1 | 5/2009 |
| EP | 2 990 072 A1 | 3/2016 |
| JP | 48-93192 A | 12/1973 |
| JP | 2009-138010 A | 6/2006 |
| JP | 2009138010 A * | 6/2009 |
| JP | 2009-254814 A | 11/2009 |
| JP | 2009254814 A * | 11/2009 |
| JP | 2010-529150 A | 8/2010 |
| WO | WO 92/03480 A1 | 3/1992 |
| WO | WO 2008/004597 A1 | 1/2008 |
| WO | WO 2008/013282 A1 | 1/2008 |
| WO | WO 2008/020632 A1 | 2/2008 |

OTHER PUBLICATIONS

Dong (Polymer Bulletin, vol. 49, 189-195 (2002)).*
Andrade et al (International Journal of Carbohydrate Chemistry, 2011, vol. 2011, pp. 1-14).*
International Search Report issued Aug. 5, 2014 in PCT/JP2014/064836 (with English language translation).
Extended European Search Report issued Sep. 27, 2016 in Patent Application No. 14807112.9.
Raphael Riva, et al. "Chitosan and Chitosan Derivatives in Drug Delivery and Tissue Engineering", Adv Polym Sci, vol. 244, XP002761807, 2011, pp. 19-44.
Suzanne M. Bal et al., Microneedle-Based Transcutaneous Immunisation in Mice with N-Trimethyl Chitosan Adjuvanted Diphtheria Toxoid Formations, Pharm Res., 2010, 27(9), p. 1837-1847.

* cited by examiner

*Primary Examiner* — Mark V Stevens
(74) *Attorney, Agent, or Firm* — Oblon, McClelland, Maier & Neustadt, L.L.P.

(57) ABSTRACT

An acicular body includes a support base, and a needle formed on the support base and containing a chitosan derivative.

20 Claims, 1 Drawing Sheet

ACICULAR BODY

CROSS-REFERENCE TO RELATED APPLICATIONS

The present application is a continuation of International Application No. PCT/JP2014/064836, filed Jun. 4, 2014, which is based upon and claims the benefits of priority to Japanese Application No. 2013-119915, filed Jun. 6, 2013. The entire contents of these applications are incorporated herein by reference.

BACKGROUND OF THE INVENTION

Field of the Invention

The present invention relates to an acicular body, and more specifically, an acicular body which is formed containing chitosan.

Discussion of the Background

A percutaneous absorption method, which is a method for penetrating a substance such as drug to be delivered into the body through the skin so that the substance to be delivered is administered into the body, is used as a convenient way of painless administration of the substance to be delivered.

In the field of percutaneous administration using a percutaneous absorption method, a technique has been proposed in which an acicular body having a needle which is sized in the order of micrometers is used to pierce the skin, thereby administering a substance to be delivered such as drug into the skin (see PTL 1).

A method for manufacturing the acicular body has been proposed, in which an original plate is manufactured by machine processing, the original plate is used to fabricate a transfer plate, and the transfer plate is used for transfer molding (see PTL 2).

Another method for manufacturing the acicular body has been proposed, in which an original plate is manufactured by etching, the original plate is used to fabricate a transfer plate, and the transfer plate is used for transfer molding (see PTL 3).

The acicular body is preferably made of a material that is harmless to the body even if a broken piece of the acicular body remains in the body. Accordingly, biocompatible materials such as chitin and chitosan are proposed as materials for the acicular body (see PTL 4).

Chitin is a component contained in the shell of crabs and shrimps, and chitosan is a deacetylated chitin. Although chitin and chitosan are not explicitly divided, at least 70% deacetylated chitin is defined as chitosan.

Chitosan has a property of being insoluble in water but soluble in acidic aqueous solution. Accordingly, an acicular body made of chitosan can be manufactured by allowing water to be evaporated from the aqueous solution.

PTL 1: JP-A-S48-93192
PTL 2: WO 2008/013282
PTL 3: WO 2008/004597
PTL 4: WO 2008/020632

SUMMARY OF THE INVENTION

According to one aspect of the present invention, an acicular body includes a support base; and a needle formed on the support base and including a chitosan derivative.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE EMBODIMENTS

Figure 1:
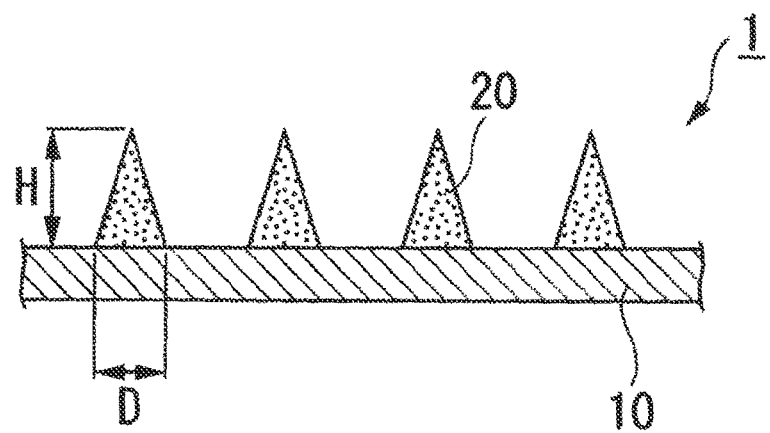
FIG. 1 is a schematic view which shows an acicular body according to one embodiment of the present invention.

The embodiments will now be described with reference to the accompanying drawings, wherein like reference numerals designate corresponding or identical elements throughout the various drawings.

With reference to FIGS. 1 to 4, one embodiment of the present invention will be described. First, a configuration of an acicular body according to this embodiment will be described.

As shown in FIG. 1, an acicular body 1 of this embodiment includes a support base 10 and a needle 20 formed on the support base 10.

The support base 10 is a film made of a resin. The support base 10 may be made of any material having a mechanical strength sufficient to support the needle 20 and may be, for example, cellophane, polyethylene, polypropylene or polyimide.

The material for the support base 10 is not limited to resin, and may be a material containing a chitosan derivative having the same composition as that of the needle 20. If the support base and the needle are made of the same composition, the support base and the needle can be integrally formed in an advantageous manner.

The support base 10 may be a multiple layer structure made up of a plurality of different materials. If the support base is provided with multiple layers made up of a plurality of different materials, it may take advantage of physical properties of a plurality of materials.

For example, (1) the support base having an upper layer adjacent to the needle 20 which is made of the same composition as that of the needle 20 and a lower layer which is made of a flexible material, (2) the support base having the upper layer made of a material having a malleability larger than that of the lower layer located on the opposite side of the upper layer, and (3) the support base having the upper layer made of a material having a contractibility smaller than that of the lower layer can be advantageously rolled into a roll shape. Accordingly, when the support base is wound around an outer peripheral surface of a cylindrical or columnar support body, a roller having a plurality of outwardly extending needles can be formed.

Further, (4) the support base having a lowermost layer formed as a flexible layer has an advantage that the needle can be protected from being damaged when a plurality of acicular bodies are stacked for storage. An adhesive layer such as an adhesive sheet may be used for stabilization of layers during stacking of the layers.

The needle 20 is formed containing chitosan derivative, and is dissolved and disappears after the needle pieces the skin. The needle 20 contains or includes a desired substance to be delivered so that the substance to be delivered is percutaneously introduced into the body as the needle is dissolved in the skin.

Examples of chitosan derivative which forms the needle 20 may be chitosan succinamide, carboxymethyl chitosan, trimethyl chitosan, either alone or a mixture thereof. Those chitosan derivatives do not require acidic compound or acidic aqueous solution for dissolution, and are easily soluble in water.

The chitosan derivatives may include chitosan derivatives derived from crustaceans such as crabs and shrimps, chitosan derivatives derived from plants of mycelium or microbial production, and chitosan derivatives prepared by using those materials as starting materials. The chitosan derivatives have advantageous effects such as a bactericidal effect and sterilizing effect as well as an aesthetic effect to the skin.

The needle 20 preferably contains a chitosan derivative as a main component. The needle 20 preferably contains 60 wt % or more of chitosan derivative. The needle 20 preferably contains 60 wt % or more of chitosan succinamide. The needle 20 preferably contains 60 wt % or more of carboxymethyl chitosan. The needle 20 preferably contains 60 wt % or more of trimethyl chitosan.

The needle 20 is preferably essentially formed of a chitosan derivative. The needle 20 preferably contains 90 wt % or more of chitosan derivative. The needle 20 preferably contains 90 wt % or more of chitosan succinamide. The needle 20 preferably contains 90 wt % or more of carboxymethyl chitosan. The needle 20 preferably contains 90 wt % or more of trimethyl chitosan.

Each needle 20 may be in any shape as long as it can pierce the skin, and may be various shape such as a cone, pyramid, cylinder, prism or pencil-like shape (a shape having a column body and a cone-shaped end portion).

A single needle 20 may be provided on the support base 10, or alternatively, a plurality of needles 20 may be disposed closely together on the support base 10. When a plurality of needles 20 are disposed, the needles 20 are preferably arranged in array. The term "array" as used herein means that the needles are arranged in a specific pattern, for example, in a matrix arrangement, close-packed arrangement, concentric circle arrangement, or random arrangement.

A hole may be formed at a distal end of the needle 20. The hole may or may not penetrate through the support base 10 in a thickness direction.

The needle 20 has dimensions of thickness and length suitable for creating a puncture hole into skin. Specifically, the needle 20 preferably has a height H in the range of 10 µm to 1000 µm. The height H refers to a length from a surface of the support base 10 to a tip of the needle 20.

The height H of the needle 20 may be determined within the above range depending on a desired depth of the puncture hole made by the acicular body piercing the skin.

For example, when a puncture hole made by the acicular body 1 piercing the skin is desired to be within the stratum corneum, the height H is preferably in the range of 10 µm to 300 µm, and more preferably, in the range of 30 µm to 200 µm.

Alternatively, when a puncture hole is desired to have a depth that penetrates through the stratum corneum and does not reach the nerve plexus, the height H is preferably in the range of 200 µm to 700 µm, more preferably, in the range of 200 µm to 500 µm, and further preferably, in the range of 200 µm to 300 µm.

When a puncture hole is desired to have a depth that reaches the dermis, the height H is preferably in the range of 200 µm to 500 µm.

Alternatively, when a puncture hole is desired to have a depth that reaches the epidermis, the height H is preferably in the range of 200 µm to 300 µm.

The needle 20 preferably has a width D in the range of 1 µm to 300 µm. The width D may be determined within the above range depending on a desired depth of the puncture hole made by the acicular body piercing the skin.

The width D is a maximum dimension of a portion of the needle which is in contact with the support base when the needle is projected in parallel to a plane of the support base 10. For example, when the needle is a conical or columnar shape, the width D is the diameter of the circular portion of the needle which is in contact with the support base. When the needle is a regular quadrangular pyramid shape or regular quadrangular prism shape, the width D is the diagonal length of the square portion of the needle which is in contact with the support base.

The needle 20 preferably has an aspect ratio in the range of 1 to 10. An aspect ratio A is defined as $A=H/D$, where H is a height and D is a width of the needle.

When the needle 20 has a tip angle of a cone-shaped portion and is used to penetrate through the stratum corneum, the tip angle $\theta$ of the needle is preferably in the range of 5 to 30 degrees, and more preferably, in the range of 10 to 20 degrees. The tip angle $\theta$ is a maximum angle (apex angle) when the needle 20 is projected parallel to a plane of the support base 10.

The substance to be delivered contained in the needle 20 may include peptides and proteins of a variety of vaccines, pharmacological active agents, cosmetic compositions and the like.

Pharmacological active agents may be selected as appropriate depending on the applications. For example, vaccines against influenza, analgesics for cancer patients, insulins, biologic agents, gene therapy agents, injection agents, oral agents or skin applying agents may be used. Since the acicular body according to the present embodiment pierces the skin, it can be applied to pharmacological active agents that need to be administered by subcutaneous injection besides the pharmacological active agents used for the conventional percutaneous administration. In particular, since injection agents such as vaccines can be administered painlessly by using the acicular body, the acicular body is suitable for use with children. Further, children have difficulty in swallowing an oral medication in the conventional way of administration. Since there is no need of swallowing a medication if the acicular body is used for drug administration, the acicular body is suitable for use with children.

If the substance to be delivered is a vaccine or the like, enhancement of the effect of substance to be delivered due to adjuvant action of chitosan can also be expected.

The cosmetic compositions are compositions used for cosmetics or beauty products. For example, they may include moisturizing agents, coloring materials, fragrances, and biologically active substances that produce beauty effects (beneficial effects for wrinkles, acne, stretch marks and the like, and mitigating effect on hair loss). When an aromatic material is used as a cosmetic composition, favorable fragrance can be added to the acicular body. This is suitable for use as a beauty product.

The substance to be delivered may be bonded to the side-chain functional group of chitosan derivative. If the substance to be delivered is bonded to the side-chain functional group, poorly soluble drugs or unstable drugs can also be advantageously delivered into the body. The substance to be delivered and the side-chain functional group of chitosan derivative are preferably bonded by an ester bond. By using an ester bond, the bond is cleaved by in vivo enzyme such as esterase after the substance to be delivered is dissolved in the body, thereby allowing the drug to exhibit an effect, that is, working as a prodrug.

In addition, the needle which contains the substance to be delivered can be manufactured by mixing the substance to be delivered with a needle-forming solution, which will be described later, or alternatively, the substance to be delivered can be loaded on the needle by applying the substance to be delivered on the surface of the needle.

An example of manufacturing method of the acicular body 1 having the above configuration will be described.

First, an intaglio plate used for forming the needle is prepared. The original plate that defines the shapes of a plurality of needles 20 is manufactured. Then, the intaglio plate is manufactured by inverting the shapes of protrusions and recesses of the original plate. The original plate may be manufactured by a known method depending on the shapes of the needles, and may be manufactured by using micromachining technique. Examples of micromachining techniques may include lithography, wet etching, dry etching, sandblasting, laser machining and precision machining. The intaglio plate may be manufactured by a known transfer molding method by using the original plate. For example, the intaglio plate made of Ni may be manufactured by a Ni electroforming method, or the intaglio plate may be manufactured by transfer molding using melted resin.

Figure 2:
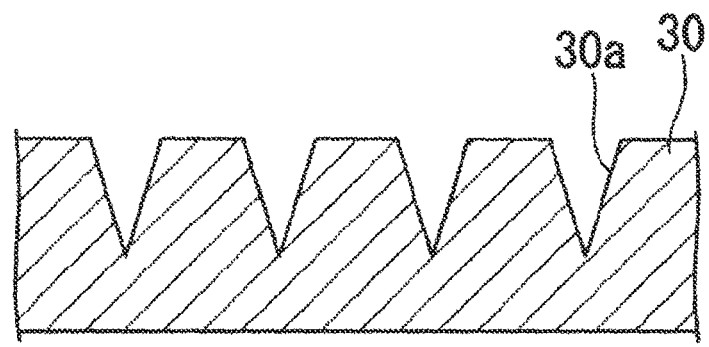
FIG. 2 is a view which shows a process of manufacturing method of the acicular body according to one embodiment of the present invention.

As shown in FIG. 2, an intaglio plate 30 having recesses 30a which correspond to the needles 20 are formed by the above procedure.

Then, the needle-forming solution which contains a chitosan derivative as a needle material is prepared. Since the chitosan derivative is soluble in water without using an acid, the needle-forming solution is readily prepared by using water as solvent. The needle-forming solution preferably has a fluidity of such an extent that allows it to be suitably filled in the recesses 30a of the intaglio plate 30 by adjusting the amount of solute as appropriate, and the needle-forming solution may be in the form of a gel.

Figure 3:
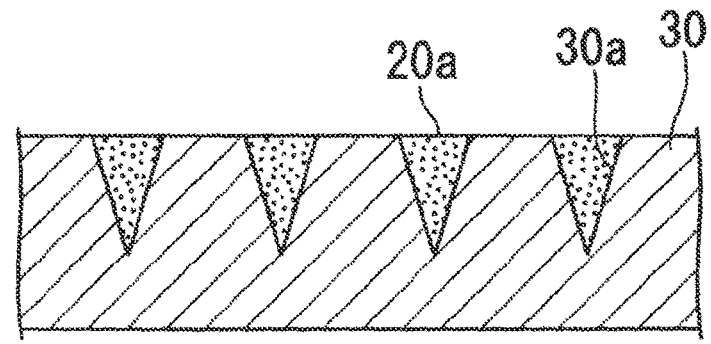
FIG. 3 is a view which shows a process of manufacturing method of the acicular body according to one embodiment of the present invention.

Then, as shown in FIG. 3, the needle-forming solution 20a is supplied onto the intaglio plate 30. A supplying method can be appropriately selected from known methods, taking into consideration the shape or dimensions of the intaglio plate 30. For example, methods such as spin coating method, method using a dispenser, a casting method and an ink-jet method can be used. Although the needle-forming solution 20a may be supplied to the intaglio plate 30 under an ordinary pressure, the needle-forming solution 20a may also be supplied under a reduced pressure or vacuum pressure in order to perform more advantageous filling of the recesses 30a. Preferably, the amount of the needle-forming solution 20a is such an extent that allows it to cover all the recesses 30a.

Then, the liquid component is removed from the needle-forming solution 20a, and the needle-forming solution 20a is solidified to form the needles 20.

This process can be performed by drying the needle-forming solution 20a while holding the intaglio plate 30 under a room temperature. Preferably, the needle-forming solution 20a is heated and dried by heating the intaglio plate 30 in order to shorten the required time. The heating method is not specifically limited, and, for example, a hotplate can be used so that the intaglio plate 30 is placed thereon.

Figure 4:
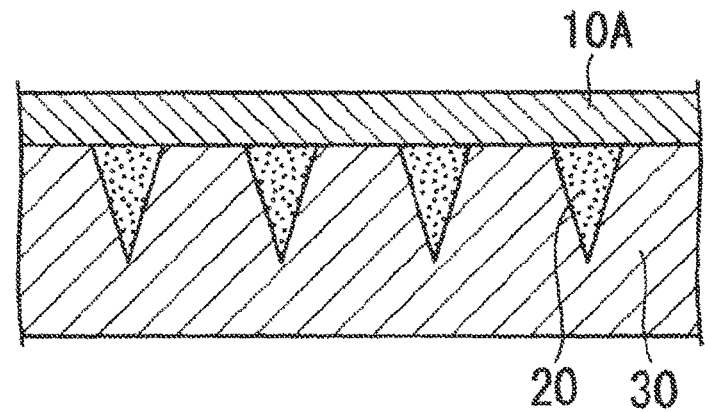
FIG. 4 is a view which shows a process of manufacturing method of the acicular body according to one embodiment of the present invention.

As shown in FIG. 4, after the needles 20 are formed, a film 10A which serves as the support base 10 is placed on the intaglio plate 30. An adhesive layer or the like is disposed on the surface of the film 10A so that the needles 20 are adhered to the film 10A. When the film 10A is peeled off from the intaglio plate 30, the needles 20 are removed along with the film 10A from the intaglio plate 30. Accordingly, the acicular body 1 having the support base 10 and the needles 20 are manufactured.

The intaglio plate 30 may be chemically dissolved instead of being peeled off as described above so as to separate the needles 20.

After completion of the acicular body 1, the acicular body 1 may be punched out to form a desired size and shape according to the application. A punching blade such as Thomson blade may be used for punching. Alternatively, the acicular body 1 may be punched out along with the intaglio plate 30 before the film 10A is peeled off from the intaglio plate 30.

An adhesive may be applied on the periphery of the needles to provide an acicular body that can be pasted on the skin or the like. An adhesive is preferably made of a material suitable for adhesion on the skin, and is further preferably made of a material that can be treated by a sterilization process.

The above manufacturing method is merely one example, and various modifications can be made.

For example, without using the film 10A, the needle-forming solution may be supplied so that a certain amount overflows from the recesses 30a to form a layer on the intaglio plate 30. When the needle-forming solution is solidified, the acicular body having the support base 10 made of the same material as that of the needles 20 may be manufactured. The material for the support base may not be completely the same as that of the needle. A material such as that containing the above chitosan and reducing sugar may be separately added after the needle-forming solution is supplied, and may be solidified with the needle-forming solution.

When the substance to be delivered is bonded to the side-chain functional group of chitosan derivative, the substance to be delivered is mixed with and dissolved in the needle-forming solution. If an organic solvent such as DMSO (dimethyl sulfoxide) is necessary for dissolution of the substance to be delivered, the organic solvent can be removed by dialysis or the like after the substance to be delivered is dissolved and bonded to the side-chain functional group to prevent the residue of organic solvent in the resultant needles.

As described above, according to the manufacturing method of the acicular body of the present embodiment, since the needles are formed by using the chitosan derivative, the needle-forming solution can be prepared without using an acid while using a highly biocompatible chitosan. As a result, a wide range of substances to be delivered can be combined, thereby achieving high versatility and biocompatibility.

The acicular body according to the present embodiment can pierce the skin with the needle, thereby penetrating the substance to be delivered such as drug for delivery of the substance to be delivered into the body. In the acicular body according to the present embodiment which includes the needle formed containing the chitosan derivative, since the needle can be hard and is not dissolved immediately when it is exposed to liquid, it may easily pierce the skin. Therefore, the acicular body according to the present embodiment can reliably pierce the skin even if water remains on the skin. For example, even immediately after bathing, the acicular body can reliably penetrate the substance to be delivered into the skin to deliver the substance to be delivered into the body.

Further, in the acicular body according to the present embodiment which includes the needle formed containing the chitosan derivative, water can be supplied to the needle before the acicular body pierces the skin in order to improve a dissolution speed of the needle of the acicular body in the body after the acicular body pierces the skin. In general, the chitosan derivative used for the acicular body of the present embodiment has a slower dissolution speed in the body compared to the other materials used as a material for acicular body. Accordingly, the dissolution speed of the needle of the acicular body in the body can be adjusted by supplying water to the needle before the acicular body pierces the skin or piercing the skin by the acicular body with water remaining on the surface of the skin.

While the manufacturing method of the acicular body according to an embodiment of the present invention will be further described with reference to examples and comparative examples, the technical scope of the present invention is not limited in any way by these examples and comparative examples.

Example 1

Manufacturing of Intaglio Plate

An original plate for the acicular body was formed so that 36 regular quadrangular pyramids (height: 150 μm, bottom: 60 μm×60 μm) were arrayed in a matrix of 6 rows by 6 columns with a pitch of 1 mm on the original plate by using a micromachining of a silicon substrate. The acicular body original plate was coated with a nickel film by plating in the thickness of 500 μm. Then, the silicon substrate was wet-etched with potassium hydroxide solution of weight percent concentration of 30% which was heated to 90° C. to manufacture an intaglio plate made of nickel and having 36 recesses.

<Preparation of Needle-Forming Solution>

Chitosan succinamide was dissolved in water to prepare chitosan succinamide solution of weight percent concentration of 5% (5 wt %).

<Manufacturing of Acicular Body>

The needle-forming solution 20a was filled into the recesses 30a of the intaglio plate 30 by using a spin coating method, and was further supplied so as to form a layer on the intaglio plate 30. The intaglio plate 30 was heated at a temperature of 120° C. for a period of 10 minutes by using a heat source so that the needle-forming solution 20a was dried and solidified. A hotplate was used as the heat source 13.

After the solidifying process, the needle-forming solution which was solidified in the form of layer was held and removed from the intaglio plate 30 to manufacture the acicular body of Example 1 which includes the support base 10 and needle 20 made of the component of the needle-forming solution.

Example 2

The acicular body of Example 2 was manufactured by the same procedure as that of Example 1, except that 5 wt % carboxymethyl chitosan solution was used as the needle-forming solution.

Example 3

The acicular body of Example 3 was manufactured by the same procedure as that of Example 1, except that 5 wt % trimethyl chitosan solution was used as the needle-forming solution.

Reference Example 1

The acicular body of Reference example 1 was manufactured by the same procedure as that of Example 1, except that a mixture of chitosan and water (chitosan 5 wt %) was used. However, manufacture of the acicular body faded since chitosan was not soluble in water.

Examples 4 and 5 are examples using the acicular body as a prodrug, in which the substance to be delivered is bonded to chitosan derivative by an ester bond.

Example 4

Manufacturing of Intaglio Plate

The same intaglio plate as that of Example 1 was used.
<Manufacturing of Needle-Forming Solution>

Chitosan succinamide was dissolved in water to prepare chitosan succinamide solution of 5 wt %.

Chloramphenicol (drug) was dissolved in DMSO to prepare chloramphenicol DMSO solution of 5 wt %.

Chitosan succinamide solution and chloramphenicol DMSO solution were mixed and stirred (stirring time 2 hours).

By using DMSO/water solution as a dialysis liquid, unreacted chloramphenicol, that is, chloramphenicol which is not ester-bonded, was separated from the stirred solution by using a dialysis membrane. Then, DMSO was removed by using water as a dialysis liquid to obtain the needle-forming solution.

After that, the acicular body of Example 4 was manufactured by the same procedure as that of Example 1.

Example 5

The acicular body of Example 5 was manufactured by the same procedure as that of Example 4, except that the 5 wt % carboxymethyl chitosan solution was used in preparation of the needle-forming solution.

Example 6

The acicular body of Example 6 was manufactured by the same procedure as that of Example 4, except that the 5 wt % trimethyl chitosan solution was used in preparation of the needle-forming solution.

Comparative Example 1

The acicular body of Comparative example 1 was manufactured by the same procedure as that of Example 1, except that chitosan solution in which chitosan was dissolved in 0.1% hydrochloric acid (chitosan 5 wt %) was used as the needle-forming solation.

(Confirmation Experiment 1)

A confirmation experiment of dissolution of the acicular body was conducted for Examples and Comparative example by using phosphate buffer solution (PBS) of pH7.5 and an artificial skin.

In the acicular body of Examples 1 to 6, the needle was dissolved without retaining the original shape after it was immersed in PBS. Further, in the acicular body of Examples 1 to 6, the needle was observed to be dissolved without retaining the original shape when 10 minutes elapsed after it was pierced into the artificial skin.

Although the acicular body of Comparative example 1 was also dissolved, acidic aqueous solution or acidic compound was required in manufacture of the acicular body.

(Confirmation Experiment 2)

The acicular body of Examples 4, 5 and 6 were dissolved in water. This solution was referred to as "test liquid 1." Further, esterase was added to the solution in which the acicular body of Examples 4, 5 and 6 were dissolved in water and was left for 2 hours. This liquid was referred to as "test liquid 2."

The resultant test liquid 1 and the test liquid 2 were analyzed by high performance liquid chromatography (HPLC). It was found that the detected amount of chloramphenicol in the test liquid 2 was 10 times or more of the detected amount of chloramphenicol in the test liquid 1 for all the Examples 4, 5 and 6.

Although chloramphenicol was added to water in an attempt to dissolve, it was not dissolved. It was confirmed that an aqueous solution failed to be prepared.

As described above, it was revealed that, according to the present invention, the acicular body which was soluble in water can be manufactured even if the substance to be delivered that was not easily soluble in water was used. Further, the substance to be delivered was bonded to the chitosan derivative contained in the acicular body by an ester bond, and was released from chitosan derivative by an effect of esterase.

(Confirmation Experiment 3)

Two pieces of the acicular bodies were prepared by the same manufacturing method as above, except that a few drops of Evans Blue (blue pigment) were added to chitosan succinamide solution used in Example 1. One of the acicular bodies was pierced into a pig skin onto which water was sprayed by using a gardening spray, while the other was pierced into a pig skin having a dried surface without applying the above process. Both acicular bodies were removed after 30 seconds. The needle of the acicular body after being removed and the surface of the pig skin after being pierced were observed. In the acicular body which was pierced into the pig skin on which water was applied in advance, it was confirmed that the needle completely disappeared. On the other hand, in the acicular body which was pierced into the pig skin having a dried surface, it was confirmed that part of the needle remained. Further, a piercing mark of the needle was confirmed in both of observation of the surface of the pig skin onto which water was applied in advance after it was pierced and observation of the surface of the pig skin having a dried surface after it was pierced by using an optical microscope.

On the other hand, as a comparative experiment, the acicular body having the same shape as that of Example 1 was prepared by the same manufacturing method as that of Example 1, except that a few drops of Evans Blue (blue pigment) were added to 10 wt % hydroxypropyl cellulose solution to prepare the needle-forming solution. The acicular body made of hydroxypropyl cellulose was pierced into the pig skin onto which water was sprayed by using a gardening spray, and was removed after 30 seconds. In the removed acicular body, while the needle completely disappeared, a piercing mark of the needle was not clearly confirmed in observation of the surface of the pig skin after it was pierced by using an optical microscope. It was considered that, in the acicular body used for the comparative experiment, the needle was dissolved before it pierced the skin, since it was brought into contact with water applied on the surface of the pig skin.

While the embodiments and examples of the present invention have been described as above, the technical scope of the present invention is not limited by the above embodiments, and without departing from the spirit of the present invention, combinations of the components can be changed, or the components can be variously modified or deleted.

For example, in the acicular body of the present invention, the needles are not necessarily independent from each other, and the lower portions of the needles adjacent to the support base may be connected to each other in the form of layer.

In an acicular body made of chitosan which is manufactured by a conventional method, an acidic compound is contained in the acicular body. As a consequence, when it is dissolved in the body, substances other than the substance to be delivered and the acicular body material are also dissolved into the body. Accordingly, depending on the acid which is used, the acicular body may be harmful to the body.

Further, for the purpose of absorption into the body, it is preferable that the acicular body material does not contain an acid from the viewpoint of reducing the effect on the body and reducing the risk of interaction with the substance to be delivered.

In light of the above circumstances, the present invention has an object to provide an acicular body made of chitosan which can be manufactured without using acidic aqueous solution, acidic compound and the like.

An acicular body according to an embodiment of the present invention includes a support base, and a needle disposed on the support base and formed containing a chitosan derivative.

In an embodiment of the present invention, the chitosan derivative may include chitosan succinamide.

In an embodiment of the present invention, the chitosan derivative may include carboxymethyl chitosan.

In an embodiment of the present invention, the chitosan derivative may include trimethyl chitosan.

An acicular body according to an embodiment of the present invention may further include a substance to be delivered loaded on the needle.

In an embodiment of the present invention, the substance to be delivered may be loaded on the needle while being bonded to the chitosan derivatives by an ester bond.

Further, in an embodiment of the present invention, the substance to be delivered may include one of pharmacological active agent, peptide and cosmetic composition.

According to an embodiment of the present invention, the acicular body formed containing chitosan can be manufactured without using acidic aqueous solution or acidic compound.

INDUSTRIAL APPLICABILITY

The acicular body of the present invention can be used in various fields requiring fine acicular structure. For example, the acicular body of the present invention can be applied to MEMS devices, optical components, sample jigs, as well as the above described applications for drugs and medical treatment, cosmetics, beauty usages, and the like.

REFERENCE SIGNS LIST 1 acicular body
10 support base 10A film
20 needle
20a needle-forming solution
30 intaglio plate
30a recess Obviously, numerous modifications and variations of the present invention are possible in light of the above teachings. It is therefore to be understood that within the scope of the appended claims, the invention may be practiced otherwise than as specifically described herein.

What is claimed is:

1. An acicular body, comprising:
a support base; and
a needle formed on the support base,
wherein the needle comprises a chitosan derivative selected from the group consisting of chitosan succinamide, carboxymethyl chitosan, trimethyl chitosan, and a combination thereof, and a substance such that the substance is delivered into a skin when the needle pierces the skin.

2. The acicular body according to claim 1, wherein the chitosan derivative comprises chitosan succinamide.

3. The acicular body according to claim 1, wherein the chitosan derivative comprises carboxymethyl chitosan.

4. The acicular body according to claim 1, wherein the chitosan derivative comprises trimethyl chitosan.

5. The acicular body according to claim 1, wherein the substance is bound to the chitosan derivative by an ester bond.

6. The acicular body according to claim 5, wherein the substance is selected from the group consisting of a pharmacological active agent, a peptide, a cosmetic composition, and combinations thereof.

7. The acicular body according to claim 1, wherein the support base comprises a resin.

8. The acicular body according to claim 1, wherein the support base comprises the chitosan derivative in the needle.

9. The acicular body according to claim 1, wherein the needle includes the chitosan derivative in an amount of 60 wt % or more.

10. The acicular body according to claim 1, wherein the needle has a hole at a distal end of the needle.

11. The acicular body according to claim 1, wherein the needle has a height in a range of from 10 µm to 1000 µm.

12. The acicular body according to claim 1, wherein the needle has a height in a range of from 30 µm to 200 µm.

13. The acicular body according to claim 1, wherein the needle has a height in a range of from 200 µm to 300 µm.

14. The acicular body according to claim 1, wherein the support base comprises a plurality of layers each having a different composition.

15. The acicular body according to claim 1, wherein the needle has a cone shape, a pyramid shape, a cylinder shape, a prism shape, or a pencil-like shape.

16. The acicular body according to claim 1, wherein the needle is prepared by a process comprising dissolving the chitosan derivative in water such that a needle-forming solution which is free of an acidic compound is formed, supplying the needle-forming solution on a plate having a plurality of recesses each having a shape of the needle, and drying the needle-forming solution.

17. The acicular body according to claim 6, wherein the pharmacological active agent is at least one selected from the group consisting of an influenza vaccine, an analgesic, insulin, a biologic agent, a gene therapy agent, an injection agent, an oral agent, and a skin applying agent.

18. The acicular body according to claim 1, wherein the substance is applied on a surface of the needle.

19. The acicular body according to claim 1, wherein the needle includes the chitosan derivative in an amount of 90 wt % or more.

20. The acicular body according to claim 1, wherein the needle is prepared by a process comprising dissolving the chitosan derivative in water such that a needle-forming solution which is free of an acidic compound is formed, and drying the needle-forming solution to form the needle.

* * * * *